(12) United States Patent
Berger et al.

(10) Patent No.: US 7,374,559 B2
(45) Date of Patent: May 20, 2008

(54) HAND-HELD DEVICE ENABLING ACCURATE DISPENSING OF A DROP OF A LIQUID INTO THE EYE OF A SUBJECT

(76) Inventors: Steven T. Berger, 70 Silver Birch Rd., Longmeadow, MA (US) 04406;
Richard P. Gibralter, 18 Pheasant Run, Scarsdale, NY (US) 10583

( * ) Notice: Subject to any disclaimer, the term of this patent is extended or adjusted under 35 U.S.C. 154(b) by 0 days.

(21) Appl. No.: 11/593,222

(22) Filed: Nov. 6, 2006

(65) Prior Publication Data

US 2007/0055208 A1    Mar. 8, 2007

Related U.S. Application Data

(63) Continuation-in-part of application No. 10/713,890, filed on Nov. 14, 2003, now abandoned.

(51) Int. Cl.
*A61M 35/00* (2006.01)

(52) U.S. Cl. ............... 604/294; 604/295; 604/300; 604/301; 604/302; 222/386; 222/541.9

(58) Field of Classification Search ............ 604/294, 604/295, 300, 301, 302, 118; 222/386, 541.9
See application file for complete search history.

(56) References Cited

U.S. PATENT DOCUMENTS

| 5,366,448 | A | * | 11/1994 | Basilice et al. | ............. 604/290 |
|---|---|---|---|---|---|
| 5,387,202 | A | * | 2/1995 | Baron | .................. 604/300 |
| 5,578,020 | A | * | 11/1996 | Mosley | .................. 604/295 |
| 5,618,274 | A | * | 4/1997 | Rosenthal | .................. 604/290 |
| 6,041,978 | A | * | 3/2000 | Hagele | .................. 222/420 |
| 6,090,086 | A | * | 7/2000 | Bolden | .................. 604/302 |
| 6,610,036 | B2 | * | 8/2003 | Branch et al. | .................. 604/295 |
| 2005/0107755 | A1 | * | 5/2005 | Berger et al. | .................. 604/295 |

* cited by examiner

*Primary Examiner*—Tatyana Zalukaeva
*Assistant Examiner*—Ilya Y Treyger
(74) *Attorney, Agent, or Firm*—Alix, Yale & Ristas, LLP

(57) ABSTRACT

A system for delivering a drop of liquid to an eye of a subject, wherein the instrument has a receiver to receive a liquid to be delivered to the eye of the subject, a transfer portion to receive the liquid from the receiver to advance a drop of the liquid by gravity and capillary action through a capillary tube to a lower discharge outlet whereat the drop of liquid breaks away and drops from the capillary tube, and a lid retractor supported adjacent to the discharge outlet of the capillary tube, for being pressed against the lower lid of the subject to form a cul-de-sac at the lower lid. The lower discharge outlet of the capillary tube is positioned adjacent to and above the lid retractor in a position to deposit the drop of liquid into the cul-de-sac.

11 Claims, 5 Drawing Sheets

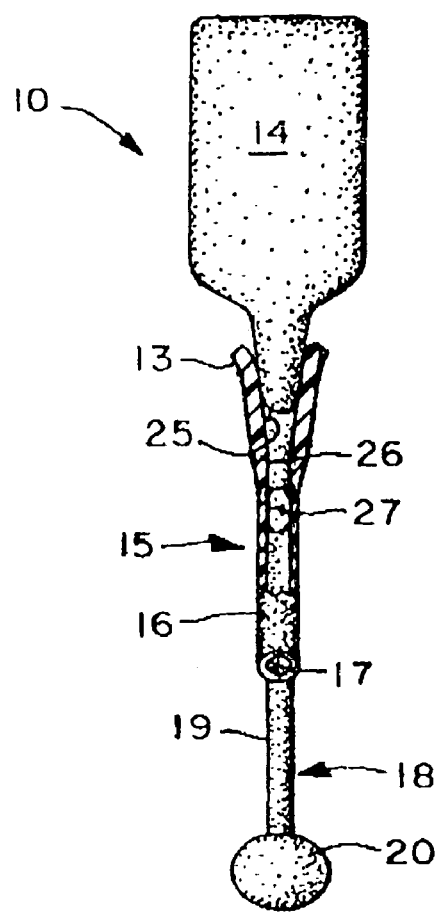
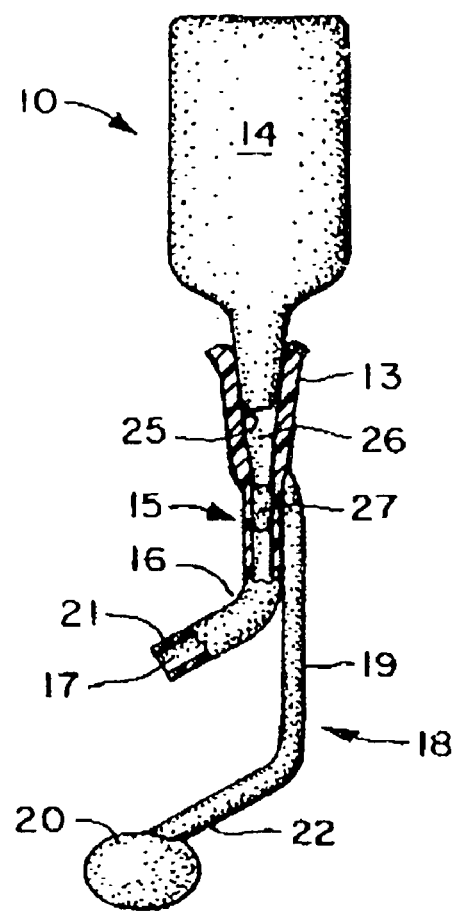
FIG. 1
FIG. 2
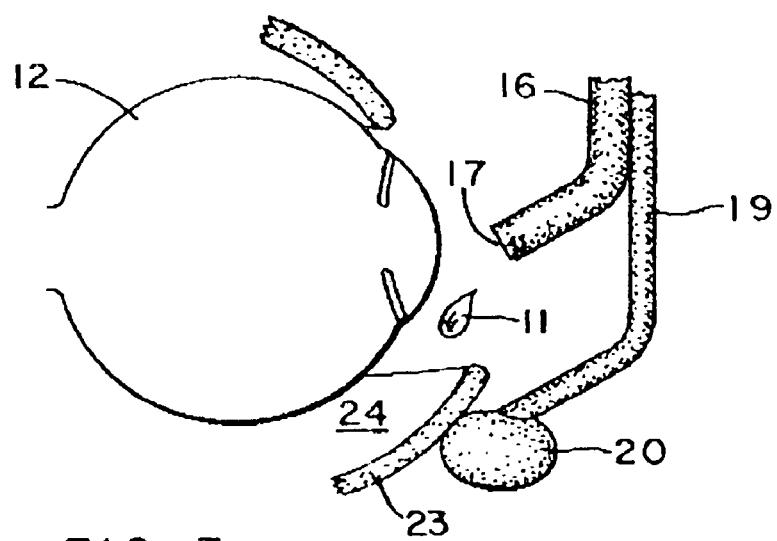
FIG. 3

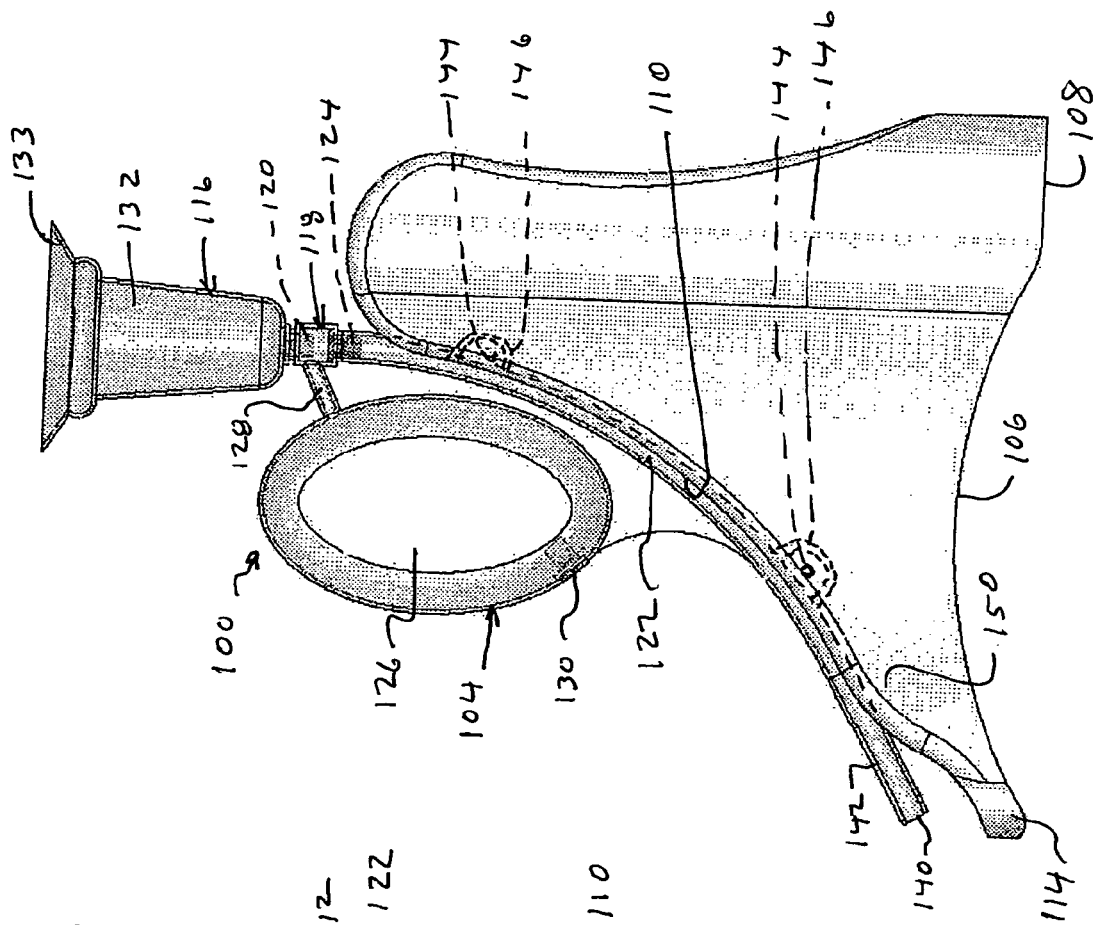
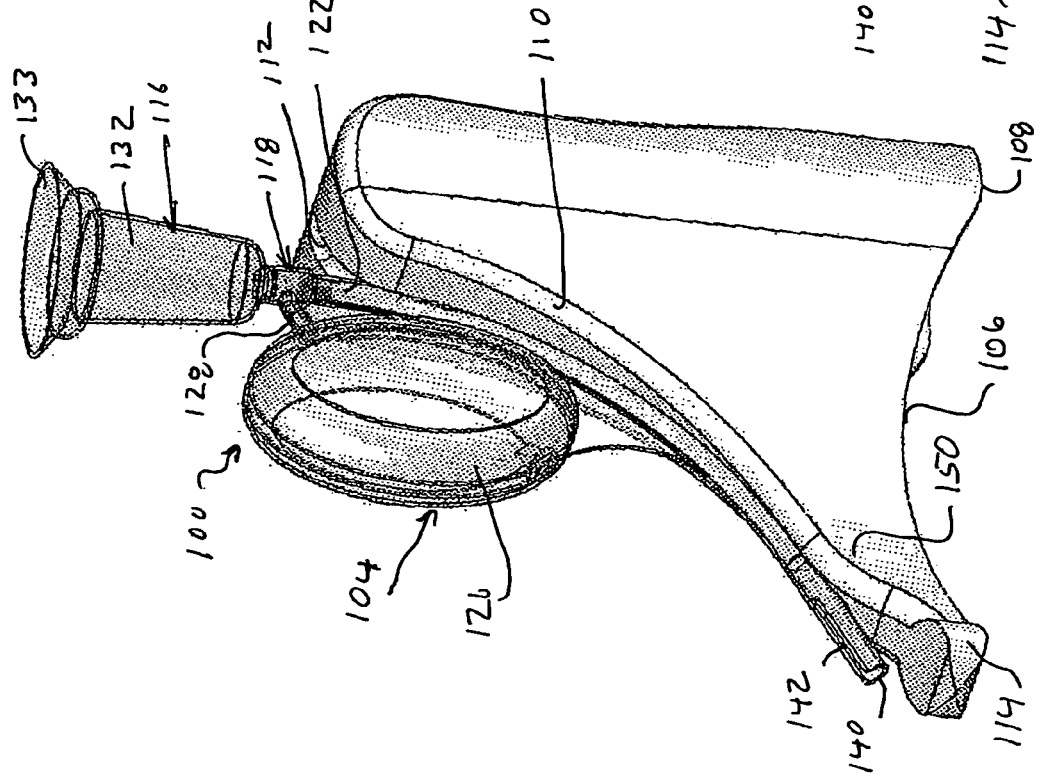

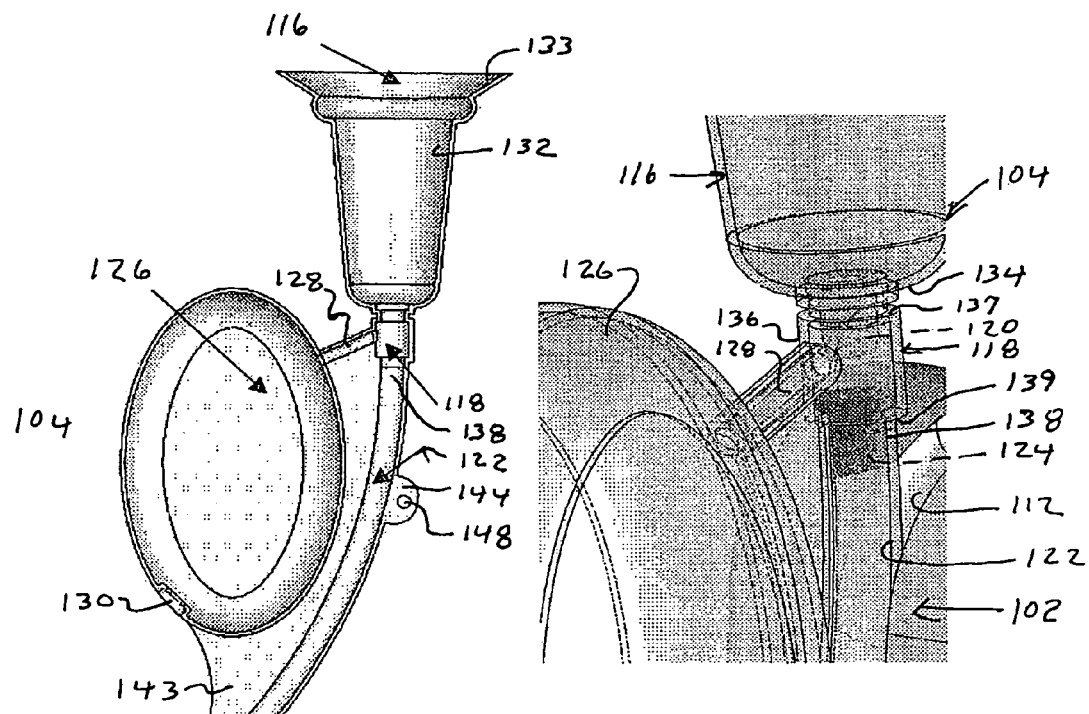
FIG. 9
FIG. 10
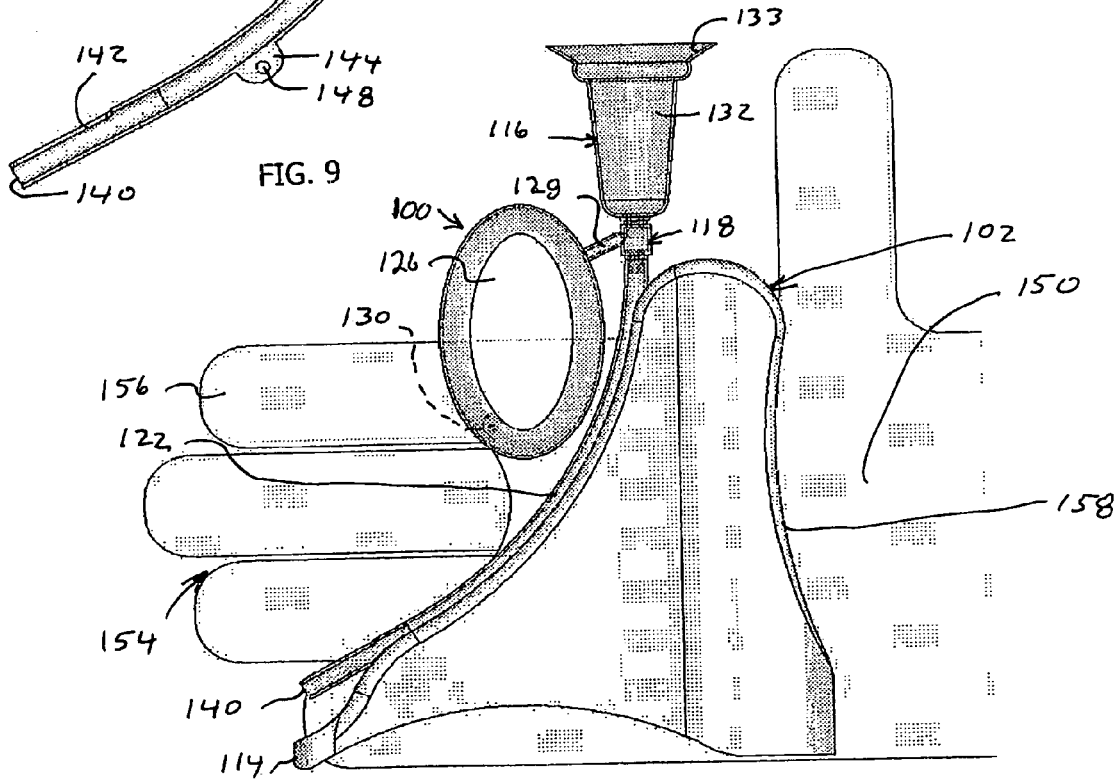
FIG. 11

HAND-HELD DEVICE ENABLING ACCURATE DISPENSING OF A DROP OF A LIQUID INTO THE EYE OF A SUBJECT

This application is a continuation-in-part of U.S. patent application Ser. No. 10/713,890 filed Nov. 14, 2003 now abandoned

FIELD OF THE INVENTION

The invention relates to an instrument and a method by which a drop of a liquid can be accurately administered by a person into his or her eye.

The invention particularly relates to such an instrument which can be operated with one hand of the person.

BACKGROUND OF THE INVENTION

Many people throughout the world are required to administer liquid drops into their eyes for a variety of purposes, such as, for administering medication to control or prevent disease, to reduce inflammation, to reduce intraocular pressure, to supply liquid tears, etc.

Current practice involves dispensing the liquid from a container dropwise into the eye of the patient by squeezing the container.

However, particularly in the case of older and disabled people, accurate dispensing of the drops into the eye of the patient is unreliable. Often such patients are unsteady in holding the eye drop dispenser, have difficulty in tilting their head back or must lie in a supine position to allow the placement of the eye drop into the patient's eye. Frequently, more than one drop is dispensed and commonly the drops are not dispensed into the eye but land on the patient's cheek resulting in widespread wastage. In the case of very expensive medications, this is costly. In brief, standard squeezable eye drop dispensers for medications or liquid tears typically dispense more than one drop when the container is squeezed and often miss their target.

SUMMARY OF THE INVENTION

An object of the present invention is to provide a device by which a drop of liquid will be dispensed accurately into the eye of the patient.

A further object of the invention is to provide such a device which can be easily handled with one hand of the patient.

Another object of the invention is to provide such a device which enables the patient to apply traction to the lower lid of the eye to expose the inferior cul-de-sac of the lower lid into which the drop of liquid is accurately dispensed.

Yet another object of the invention is to provide such a device which is inexpensive and may be disposed of after a single or several uses.

Still another object of the invention is to provide such a device which is compact and is capable of being packaged so that a number of devices can be incorporated into a package and used one by one.

The above and further objects of the invention are achieved by a device which comprises a manually held instrument having a lid retractor and a liquid conveyor integrated and arranged so that liquid introduced into the liquid conveyor is advanced as a liquid drop and deposited into the eye of the subject whose lower lid is retracted by the lid retractor.

It is a feature of the invention that the instrument is constructed so that it can be held in one hand of the user to achieve the retraction of the lower lid and the dispensing of the liquid drop into the eye of the subject.

In further accordance with the invention, the instrument has a liquid conveyor which includes a receiver for the liquid to be delivered to the instrument and a transfer portion connected to the receiver to transfer the liquid to a capillary tube in which the liquid is advanced as a drop by gravity and capillary action to a lower discharge outlet of the capillary tube. Thereat, the drop of liquid breaks away and drops from the capillary tube into the inferior cul-de-sac of the lower lid of the eye which is exposed by a lid retractor supported adjacent to the discharge outlet of the capillary tube. The lid retractor retracts the lower lid of the eye when pressed against the lower lid to form the cul-de-sac of the lower lid.

The invention is characterized in that the lower discharge outlet of the capillary tube is positioned adjacent to and above the lid retractor so that when the liquid drop falls from the outlet of the capillary tube, it will fall directly and accurately into the cul-de-sac.

According to one embodiment of the invention (heretofore referred to as embodiment one), the receiver of the instrument is formed to engage and secure a conventional liquid dispenser therein so that the liquid can be introduced into the capillary tube by squeezing the liquid dispenser which remains attached to the instrument. The dispenser and the instrument can be removably stored in a sanitary case between individual dispensing of drops. The cover can be used for color coding or otherwise identifying the contents of the dispenser.

In accordance with another embodiment of the invention (heretofore referred to as embodiment two), it is contemplated that the instrument will be a single stand-alone article into which the eye liquid can be deposited from a conventional liquid dispenser which is then disconnected. The drop then flows to the discharge outlet whereat the lid retractor will have been pressed against the lower lid to retract the lid and expose the inferior cul-de-sac.

This embodiment two, will include a holder having finger-engaging means to facilitate the handling of the instrument and the dispensing of the liquid. In addition, it will incorporate a reservoir, which can receive a quantity of liquid such that when the attached flexible bulb is pressed or squeezed, a drop of liquid will be introduced into the capillary tube.

In another embodiment of the invention, the instrument can include a holder having finger-engaging means to facilitate the handling of the instrument and the dispensing of the liquid.

It is further contemplated according to the invention, to form the receiver as a loading chamber for the liquid to which is connected a flexible air-filled bulb such that when the bulb is pressed or squeezed a drop of liquid will be dispensed from the loading chamber into the capillary tube.

The invention also contemplates a method which utilizes the instrument for manual operation by one hand of the user such that when the instrument is pressed against the lower lid of the eye to expose the cul-de-sac of the lower lid, causing a drop of liquid to flow in the instrument and drop into the cul-de-sac.

It is a feature of the invention that in order to prevent reflux of the liquid, a one-way valve is provided.

It is a further feature of the invention that the lower ends of the capillary tube and the lid retractor are bent at an angle with respect to the longitudinal extent of the capillary tube in order to position the lid retractor to expose the cul-de-sac when pressed against the lower lid and to locate the discharge outlet of the bent end of the capillary tube to dispense the liquid drop into the cul-de-sac.

According to another embodiment, an eye drop delivery system for delivering a drop of liquid to an eye of a subject may comprise a delivery apparatus having a discharge opening for delivering a drop of fluid to an eye of a subject and a stand having a lid retractor thereon for being pressed against the lower lid of the user to produce a cul-de-sac. The delivery apparatus is removably attached to said stand in a position so that the discharge opening is positioned to deposit a drop of liquid into the cul-de-sac when said lid retractor is pressed against the lower lid.

BRIEF DESCRIPTION OF THE FIGURES OF THE DRAWING

FIG. 1 is a front view, partially in section, of a first embodiment of the device according to the invention in cooperation with a liquid dispenser;

FIG. 2 is a side view of the device and dispenser of FIG. 1;

FIG. 3 shows a part of the device of FIG. 1 in an operative position in which a drop of liquid is deposited into the eye of a subject;

FIG. 7 is a perspective view of a third embodiment of a system for delivering a drop of liquid to an eye of a subject;

FIG. 8 is a side view of the system of FIG. 7;

FIG. 9 is a side view of the delivery apparatus of the system of FIG. 7;

FIG. 10 is an enlarged perspective view, partially in section, of the system of FIG. 7 showing the interconnection of the squeeze bulb, reservoirs, and delivery tube; and FIG. 11 is a side view showing the system of FIG. 7 in the palm of a hand.

DETAILED DESCRIPTION

Figure 4A:
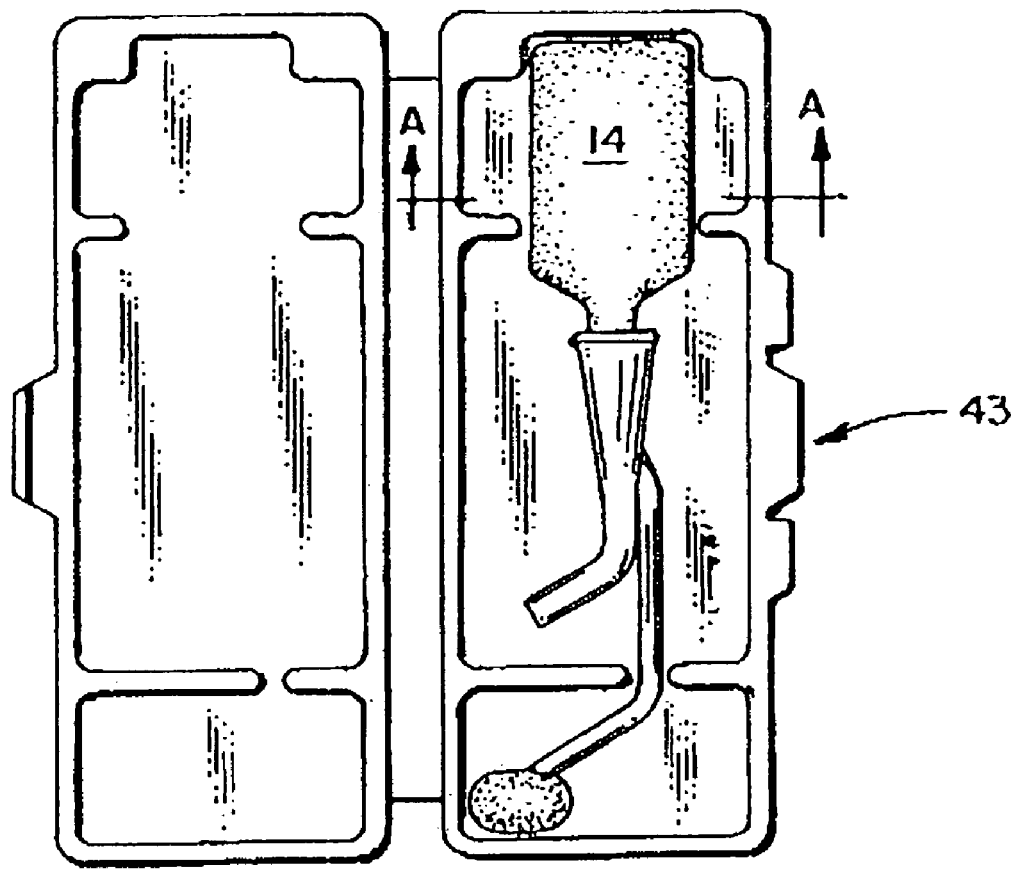
FIG. 4a is a front view of the device of FIG. 1 shown in conjunction with an opened protective case.

Referring to FIGS. 1-3, therein is shown a first embodiment (embodiment one) of an instrument 10 for delivering a drop of liquid 11 (FIG. 3) to an eye 12 of a user. The instrument 10 includes a receiver 13 of funnel shape adapted to receive the liquid from a dispenser 14. The dispenser 14 can be a conventional dispenser for an ophthalmic medication or for liquid tears, etc. By squeezing the dispenser 14, the drop of liquid is introduced into the receiver 13 of the instrument 10.

The receiver 13 is connected to a transfer portion 15 so that liquid dispensed into the receiver 13 will flow into the transfer portion 15. The transfer portion 15 includes a capillary tube 16 through which the liquid passes by capillary action and gravity to a slightly conical end with a lower discharge outlet 17. At the discharge outlet 17, the drop of liquid 11 breaks away and drops from the capillary tube as shown in FIG. 3.

Secured to the capillary tube is a lid retractor 18 which comprises a rod 19 secured to the capillary tube 16 and at the end of the rod is fixed a pressing member 20 made of a soft material which is adapted to contact and press against the lower lid of the eye of the user. An end portion 21 of the capillary tube and an end portion 22 of the lid retractor are bent at an angle to ensure accurate dispensing of the drop of liquid into the eye of the user.

In this respect, when the pressing member 20 is pressed against the lower lid 23 of the eye of the user, the lower lid is retracted to form a cul-de-sac 24 of the lower lid into which the drop 11 of liquid is deposited.

In operation, the user engages the capillary tube and presses the lid retractor against the lower lid to form the cul-de-sac 24 whereafter the drop 11 of liquid is dispensed from the dispenser and deposited into the cul-de-sac. An interior surface 25 of a channel 26 of the capillary tube is smooth and calibrated so that the liquid can easily travel thereon. A coating can be applied to the inner surface to ensure the smooth travel of the liquid, as for example, by applying a Teflon™ coating on the interior surface 25. A one-way valve 27 is provided in the capillary channel in proximity to the juncture of the capillary channel with the receiver 13 in order to prevent reflux of the liquid back into the receiver. The one-way valve 27 can be constructed as a simple flap valve which will allow passage of the liquid into the capillary channel but prevent reverse flow out of the channel.

Preferably, the instrument 10 is made of an inexpensive plastic material so that it can be disposed of even after a single use.

The construction of the described instrument 10, enables the user to deposit the drop of liquid into his or her eye without any need for the user to occupy any special position in order to dispense the liquid drop. In this respect, it is unnecessary for the user to tilt his or her head back or to lie in a supine position in order to administer the drop. The instrument is simple to use such that the liquid drop will be precisely deposited into the user's eye using one hand of the user. In this respect, when the lid retractor is pressed in proximity to the lower lid of the eye, the discharge outlet 17 of the capillary tube will automatically be positioned to deposit the drop of liquid into the cul-de-sac of the eye. It is contemplated that a drop of liquid will be dispensed from the dispenser 14 into the receiver 13 and the user will have adequate time to retract the lower lid and to dispense the liquid drop into the cul-de-sac of the eye. Alternatively, the liquid from the dispenser can be deposited into the receiver after the lid retractor has been pressed against the lower lid.

Because of the low cost of the instrument, a number of instruments can be included in a package and removed one by one for individual use.

Figure 4B:
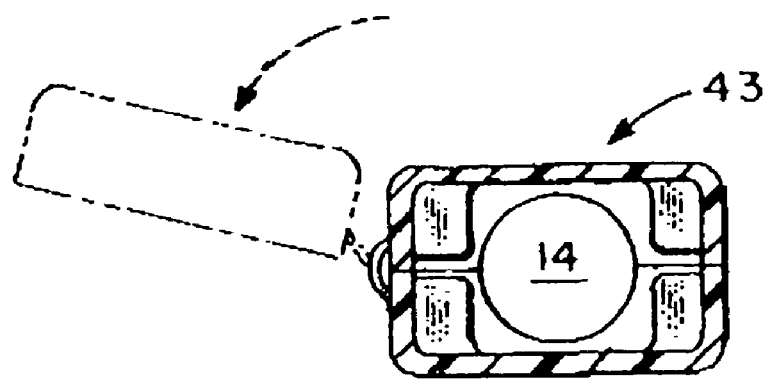
FIG. 4b is a sectional view of the device and case in a closed position taken along the line A-A of FIG. 4a with an open case portion shown in phantom.

The instrument of FIGS. 1-3 is adapted to be used for dispensing a multitude of drops until the contents of the dispenser 14 are exhausted. Therefore, a cover may be in the form of a case 43 utilized to preserve sanitary conditions between the dispensing of drops. Referring to FIGS. 4a-4b, the case is internally configured to receive both the instrument 10 and the dispenser 14 while they are maintained in a coupled pre-dispensing relationship. The case 43 is of a size to enclose the entire instrument therewithin as shown in FIGS. 4a-4b. When the instrument is to be used to dispense a drop of liquid into the user's eye, the cover 43 is opened, the instrument 10 and dispenser 14 are removed as a unit, the lid retractor is pressed against the lower lid, and the dispenser 14 is squeezed to discharge a drop of liquid into the instrument for discharge at outlet 17. The instrument and dispenser are then replaced in the case which is pivotally closed in the FIG. 4b arrow direction to maintain sanitary conditions between individual dispensing of drops. The case 43 can also be color coded or otherwise identified to indicate the contents of the dispenser. The cover or case can also assume a number of other forms.

The configuration of the discharge outlet is intended to ensure formation of the drop of liquid and its discharge into the eye of the user. Other modified forms of the discharge outlet are also within the contemplation of the invention provided they form and discharge the drop of liquid into the eye of the user.

Figure 6:
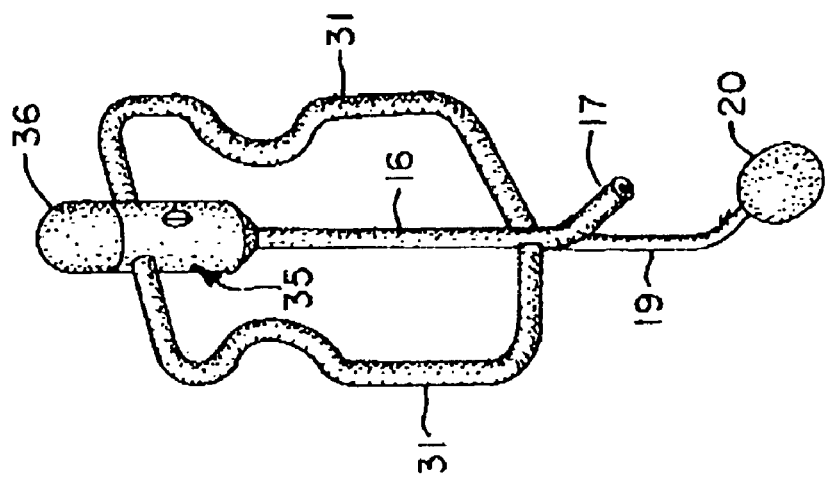
FIG. 6 is a perspective view of the modified device of FIG. 5.
Figure 5:
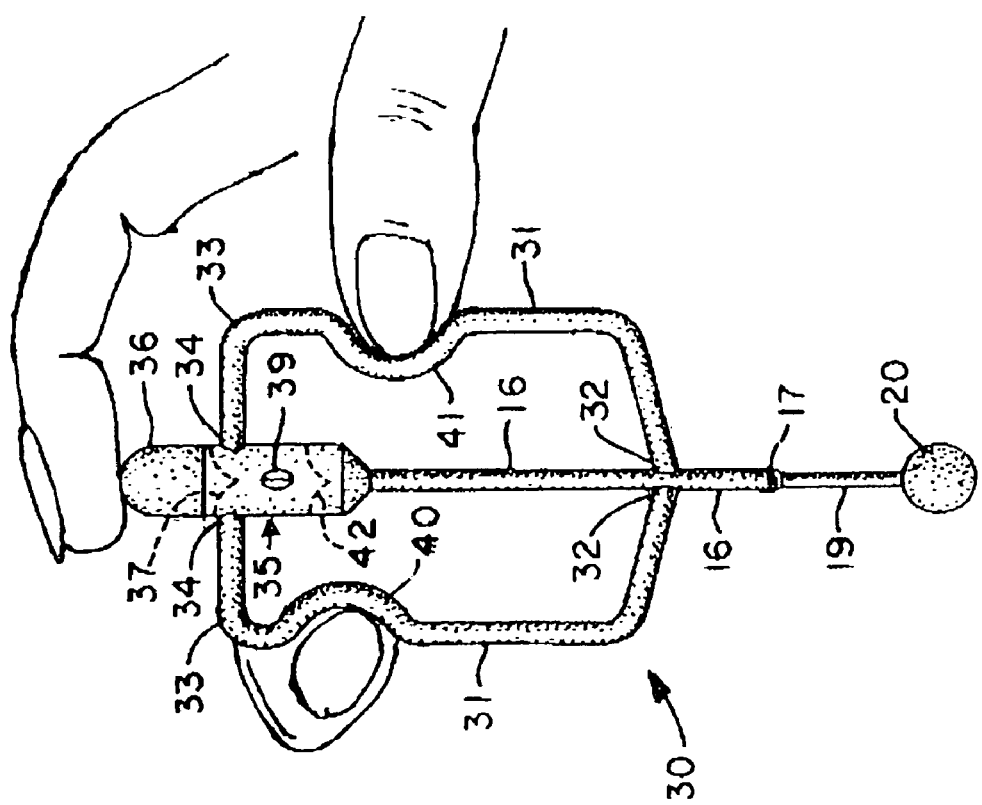
FIG. 5 is a front view of a modified device, embodiment two, shown in conjunction with the thumb and fingers of a user to illustrate the operation thereof.

FIGS. 5-6 show another embodiment, embodiment two, of the invention in which the same or similar elements in FIGS. 1-3 have the same reference numerals.

The embodiment two of FIGS. 5-6 employs a holder 30 which enables the user to retract the lower lid and dispense a drop of liquid with a one-hand operation. The holder 30 comprises two rod members 31 whose lower ends 32 are fixed to the capillary tube 16. At their upper ends the rods are bent to form portions 33 which are attached to the loading chamber at site 34. At the upper end of the capillary tube 16, there is secured a loading chamber 35 which replaces the receiver 13 in the embodiment one of FIGS. 1-3. The loading chamber 35 is connected to a deformable air-filled bulb 36 which projects beyond the bent portions 33 of the holder so that a portion of the bulb is compressed by the fingers to dispense the liquid, as will be explained subsequently. The loading chamber 35 incorporates flap valve 37 which defines the upper end of the loading chamber 35 and another flap valve 42 defines the lower end of the loading chamber. In addition, there is a cover valve 39 into which a nozzle of a dispenser (not shown) can be introduced in order to fill the loading chamber 35 with liquid.

The rods 31 are provided with internally dimpled depressions 40 and 41 which form finger-engaging recesses. A second one-way valve 42 is provided at the bottom of the loading chamber 35 at the juncture thereof with the capillary tube 16 to prevent reflux of liquid from the capillary tube.

In use, the user engages the finger-engageable portion 41 with his or her thumb and the finger-engaging portion 40 with his or her middle finger. The soft material of the pressing member 20 is then pressed against the lower lid of the eye and the flexible bulb 36 is pressed with the forefinger of the user to cause a drop of the liquid to pass from the loading chamber 35 into the capillary tube 16 to the outlet thereof to be dispensed into the cul-de-sac 24 of the lower lid.

As shown in FIG. 5, the rods 31 are rectilinear and lie in a common plane to form a flat profile for the holder 30 which is coplanar with the capillary tube.

In the embodiment two of FIG. 6, rod 19 of the lid retractor is directly connected to the bottom of the bent portion of the capillary tube.

As seen in the above, the invention provides a hand-engageable instrument for administering eye drops to the eye of the user, in which the transfer section forms a liquid flow means for dispensing the liquid one drop at a time to the discharge outlet thereof in combination with the lid retractor which exposes the cul-de-sac at the lower lid into which the liquid drop is deposited. The liquid flow portion and the lid retractor portion of the device are integrated and arranged so that the discharge outlet of the flow system is positioned to deposit the drop of liquid directly and accurately into the cul-de-sac when the lid retractor is pressed against the lower lid. The lid retractor and the liquid flow portion are so integrated and arranged that the instrument can be manually held in one hand for dispensing the liquid drop into the eye.

Another embodiment of an eye drop delivery system 100 is shown in FIGS. 7-11. In accordance with this embodiment, the eye drop delivery system 100 comprises a two piece device including a stand 102 and a delivery apparatus 104 removably attached to the stand 102.

The stand 102 may be injection molded from any suitable plastic. Referring particularly to FIGS. 7 and 8, the stand 102 includes a base 106 for supporting the stand 102 in an upright position. For this purpose, the base includes surface engaging portions 108 that are configured to contact a horizontal surface to maintain the stand 102 upright. The stand 102 also includes an arcuate concave front surface 110 having a slot 112 therein to removably receive the delivery section 104. The bottom of the front end of the stand 102 is provided with a lid retractor 114. The lid retractor 114 may be formed integrally as part of the stand 102, or may be an insert or attachment of relatively soft material.

The delivery apparatus 104 generally includes an open reservoir 116 that communicates with a closed reservoir 118 through a one-way check valve 120 such as a duckbill valve. The outlet of the closed reservoir 118 is connected to a delivery tube 122 through a second one-way check valve 124 that also may be a duckbill valve. An air filled squeeze bulb 126 is included having its outlet connected to the closed reservoir 118 by a suitable conduit 128. The squeeze bulb 126 is provided with a one-way check valve 130, such as a duckbill valve, to permit air to enter the squeeze bulb 126, but prevent air for exiting when the bulb 126 is squeezed, so that air only moves into the closed reservoir 118 when the bulb 126 is squeezed.

More specifically, the open reservoir 116 may comprise a cup-like member 132 having an open top 133 through which a drop of fluid may be deposited into the open reservoir 116. The open reservoir 116 has an opening in its bottom surface 134 in which the one-way valve 120 is positioned. As shown in FIG. 10, the closed reservoir 118 is attached to the bottom of the open reservoir 116 and may be a generally cylindrical member 136. The top 137 of the closed reservoir 118 has an opening therein communicating with the open reservoir 118 through the one-way valve 120. The conduit 128 from the squeeze bulb 126 is connected to the side of the cylinder member 136 and is in communication with the interior thereof.

The delivery tube 122 may be a pipette type capillary tube having its upper or inlet end 138 connected to the cylinder member 136 at the bottom 139 thereof and in fluid communication with the interior thereof through the second one-way valve 124. The bottom end of the delivery tube 122 comprises the discharge opening 140. A slit 142 is provided in the upper surface of the delivery tube 122 at the discharge end thereof extending in from the discharge opening 140 as shown in FIG. 7 to eliminate capillary action at the tip. The delivery tube 122 is curved in a concave arcuate manner similar to the curvature of the front of the stand 102.

The squeeze bulb 126 is integral with the delivery apparatus 104 by means of a plastic web 143 interconnecting the squeeze bulb 126, delivery tube 122 and the conduit 128 as shown particularly in FIG. 9. The squeeze bulb 126 is positioned to the front of the delivery tube as shown in the drawings and includes a substantial portion positioned below the open reservoir 116. The connecting conduit 128 extends rearward from the back side of the squeeze bulb 126 to the cylinder member 136.

As mentioned above, the delivery apparatus 104 is adapted to be removably attached to the stand 102. For this purpose, the delivery tube 122 of the delivery apparatus 104 is adapted to be received in the slot 112 in the arcuate front surface 110 of the stand. The delivery tube 122 includes a plurality of lugs 144 extending from the bottom surface thereof as particularly shown in FIG. 9. The lugs 144 are designed to be received in mating recesses 146 in the bottom of the slot 112 in the stand 102. Each lug may include a detent 148 in each side adapted to engaged a dimple (not shown for the sake of clarity) in the side wall of its corresponding recess 146 in the stand to provide a snap fit between the stand 102 and the delivery apparatus 102.

The bottom portion 150 of the front surface of the stand 102 has a generally convex shape so that the discharge opening 140 of the delivery tube 122 will extend out of the slot 112. The lugs 144 on the delivery tube 122 and the mating recesses 146 in the bottom of the slot 112 in the stand 102 serve to positively position the delivery apparatus 104 on the stand 102 so that the discharge opening 138 of the delivery tube 122 is positioned adjacent to and above the lid retractor as shown in FIG. 8.

As shown in FIG. 11, the delivery device 100 of this embodiment is designed to fit into the palm 150 of a hand 152 with the fingers 154 extending forward to overlap the system 100 with at least the forefinger 156 being in a position to engage the squeeze bulb 126. The rear surface 158 of the stand is slightly concave to conform to the curvature of the palm at the base of the thumb.

In use, the two parts, the delivery apparatus 102 and stand 102, are snapped together with the delivery tube 122 positioned in the slot 112, and the lugs 144 received in the recesses 146. A drop of the desired liquid is placed in the open reservoir 116 whereupon it flows through the one way valve 120 into the closed reservoir 118. During this loading process, the system device 100 may be placed on a flat surface and maintained in an upright position by virtue of the surface contacting portions 108 of the base 106 of the stand 102. Thus, the device does not have to be held while loading.

With the device loaded with fluid, the user may grasp the device and position the lid retractor 114 against the lower lid of the eye of the user to form a cul-de-sac into which the drop may be deposited. The user then squeezes the squeeze bulb 126 forcing air into the closed reservoir to provide driving pressure to move the fluid. The air drives the fluid from the closed reservoir 118 through the second one way valve 124 and into and down the delivery tube 122. When the drop of fluid reaches the discharge opening 138 of the delivery tube 122, the drop breaks away from the delivery tube 122 and drops into the cul-de-sac.

The first one-way valve 120 prevents any back flow of the fluid from the closed reservoir 118 into the open reservoir 116 during squeezing of the bulb 126. The second one-way valve 124 prevents any back flow of the liquid from the delivery tube into the closed reservoir when the squeeze bulb 126 is released. The one-way valve in the squeeze bulb 126 permits air to enter the interior thereof to refill the bulb 126, but prevents exit of the air during squeezing.

By virtue of the arrangement of the embodiment of FIGS. 7-11, an eye drop delivery device system is provided which can be loaded while standing in an upright position and in which the delivery portion can be easily separated from the stand when desired, such as for example for easy cleaning of the delivery apparatus.

Although the invention is disclosed with reference to particular embodiments thereof, it will become apparent to those skilled in the art that numerous modifications and variations can be made which will fall within the scope and spirit of the invention as defined by the attached claims.

What is claimed is:

1. An eye drop delivery system for delivering a drop of liquid to an eye of a subject, said system comprising:
    a delivery apparatus having a discharge opening for delivering a drop of fluid to an eye of a subject,
    a stand having a lid retractor thereon for being pressed against the lower lid of the user to produce a cul-de-sac, said delivery apparatus being removably attached to said stand in a position so that said discharge opening is positioned to deposit a drop of liquid into the cul-de-sac when said lid retractor is pressed against the lower lid,
    wherein said delivery apparatus includes a reservoir for holding a drop of fluid, a delivery tube having one end attached to said reservoir and said discharge opening at the other end, and a squeeze bulb for causing a flow of air when squeezed to move said drop of liquid from said reservoir into said delivery tube to said discharge opening, and
    wherein said stand has a slot in its forward surface, said delivery tube of said delivery apparatus being removably received in said slot.

2. The eye drop delivery system of claim 1, wherein said delivery tube has lugs thereon and said stand has mating recesses at the bottom of said slot to receive said lugs.

3. The eye drop delivery system of claim 2, wherein said lugs and recesses form a snap fit.

4. The eye drop delivery system of claim 1, wherein said forward surface of said stand is concave and arcuate, and said delivery tube which is mounted in said slot has a corresponding curvature, said lid retractor being positioned at the base of the forward end of the stand, the said forward surface adjacent the base portion being convex so that the end portion of said delivery tube extends out of said slot above said lid retractor.

5. An eye drop delivery system for delivering a drop of liquid to an eye of a subject, said system comprising:
    a delivery apparatus having a discharge opening for delivering a drop of fluid to an eye of a subject,
    a stand having a lid retractor thereon for being pressed against the lower lid of the user to produce a cul-de-sac, said delivery apparatus being removably attached to said stand in a position so that said discharge opening is positioned to deposit a drop of liquid into the cul-de-sac when said lid retractor is pressed against the lower lid,
    wherein said delivery apparatus includes a first reservoir open at its top for the reception of a drop of fluid, a second reservoir having a top and a bottom, said second reservoir being connected at its top to said first reservoir, and a delivery tube having one end attached to said bottom of said second reservoir and a discharge opening at its other end, and
    wherein said delivery apparatus further includes a squeeze bulb, said squeeze bulb communicating with said second reservoir for causing a flow of air when squeezed to move said drop of liquid from said reservoir into said delivery tube to said discharge opening.

6. An eye drop delivery system for delivering a drop of liquid to an eye of a subject, said system comprising:
    a delivery apparatus having a discharge opening for delivering a drop of fluid to an eye of a subject,
    a stand having a lid retractor thereon for being pressed against the lower lid of the user to produce a cul-de-sac, said delivery apparatus being removably attached to said stand in a position so that said discharge opening is positioned to deposit a drop of liquid into the cul-de-sac when said lid retractor is pressed against the lower lid, wherein said delivery apparatus includes a first reservoir open at its top for the reception of a drop of fluid, a second reservoir having a top and a bottom, said second reservoir being connected at its top to said first reservoir, and a delivery tube having one end attached to said bottom of said second reservoir and a discharge opening at its other end, and wherein said delivery apparatus further includes a first one-way valve between said second reservoir and said first reservoir to prevent back flow of fluid from said second reservoir into said first reservoir.

7. The eye drop delivery system of claim 6, wherein said delivery apparatus further includes a second one-way valve between second reservoir and said delivery tube to prevent backup of fluid from said delivery tube into said second reservoir.

8. The eye drop delivery system of claim 7, wherein said first and second one-way valves are duckbill valves.

9. The eye drop delivery system of claim 6, wherein said delivery tube has a slit through its surface adjacent said discharge opening.

10. The eye drop delivery system of claim 1, wherein said stand includes a base, said base adapted to support said stand in an upright position when set on a horizontal surface.

11. The eye drop delivery system of claim 10, wherein said base of said stand includes a plurality of contact portions to engage a horizontal surface to hold the stand in an upright position.

* * * * *

UNITED STATES PATENT AND TRADEMARK OFFICE
CERTIFICATE OF CORRECTION

PATENT NO. : 7,374,559 B2  
APPLICATION NO. : 11/593222  
DATED : May 20, 2008  
INVENTOR(S) : Berger et al.

Page 1 of 1

It is certified that error appears in the above-identified patent and that said Letters Patent is hereby corrected as shown below:

TITLE PG, ITEM (76) INVENTORS:

After "Steven T. Berger," delete "70 Silver Birch Rd., Longmeadow, MA (US) 04406;"

and insert --87 Brittany Lane, Somers, CT (US) 06071;--.

Signed and Sealed this

Twenty-sixth Day of August, 2008

JON W. DUDAS  
*Director of the United States Patent and Trademark Office*